(12) United States Patent
Tway

(10) Patent No.: US 6,916,763 B2
(45) Date of Patent: Jul. 12, 2005

(54) PROCESS FOR PREPARING A CATALYST FOR THE OXIDATION AND AMMOXIDATION OF OLEFINS

(75) Inventor: Cathy L. Tway, League City, TX (US)

(73) Assignee: Solutia Inc., St. Louis, MO (US)

(*) Notice: Subject to any disclaimer, the term of this patent is extended or adjusted under 35 U.S.C. 154(b) by 290 days.

(21) Appl. No.: 10/306,664

(22) Filed: Nov. 27, 2002

(65) Prior Publication Data

US 2004/0102643 A1 May 27, 2004

(51) Int. Cl.[7] .............. B01J 23/00; B01J 23/40; B01J 23/56; B01J 23/02; B01J 23/16
(52) U.S. Cl. .............. 502/300; 502/302; 502/306; 502/308; 502/311; 502/313; 502/317; 502/319; 502/321; 502/323; 502/325; 502/327; 502/329; 502/330; 502/332; 502/340; 502/344; 502/349; 502/353
(58) Field of Search ............ 502/300, 302–355

(56) References Cited

U.S. PATENT DOCUMENTS

| | | | |
|---|---|---|---|
| 3,546,138 A | | 12/1970 | Callahan et al. |
| 3,657,155 A | * | 4/1972 | Yoshino et al. ............ 502/249 |
| 4,018,712 A | * | 4/1977 | Li ............................ 502/249 |
| 4,035,410 A | | 7/1977 | Marion et al. |
| 4,065,468 A | * | 12/1977 | Grasselli et al. ........... 549/258 |
| 4,222,899 A | | 9/1980 | Innes et al. |
| 4,309,361 A | | 1/1982 | Suresh et al. |
| 4,377,500 A | | 3/1983 | Grasselli et al. |
| 4,413,155 A | | 11/1983 | Suresh et al. |
| 4,487,850 A | | 12/1984 | Li |
| 4,547,484 A | | 10/1985 | Li |
| 4,590,173 A | | 5/1986 | Sasaki et al. |
| 4,590,175 A | | 5/1986 | Sasaki et al. |
| 5,094,990 A | | 3/1992 | Sasaki et al. |
| 5,521,137 A | | 5/1996 | Martin et al. |
| 5,866,502 A | | 2/1999 | Cirjak et al. |
| 6,156,920 A | | 12/2000 | Brazdil, Jr. et al. |

FOREIGN PATENT DOCUMENTS

WO    WO 00/72962 A1    12/2000

OTHER PUBLICATIONS

Sasaki, Yutaka; Preparation and performance of iron antimonate catalysts for fluid–bed ammoxidation; Applied Catalysis A: General 194–195 (2000) 497–505 Mar. 1999.

* cited by examiner

Primary Examiner—Mark L. Bell
Assistant Examiner—Patricia L. Hailey
(74) Attorney, Agent, or Firm—Banner & Witcoff, Ltd.; John P. Foryt

(57) ABSTRACT

A process for preparing an antimonate-based mixed metal oxide catalyst in a catalytically active oxidized state, wherein the catalyst is represented by the empirical formula $Me_aSb_bX_cQ_dR_eO_f$, wherein Me, X, Q, R, a, b, c, d, e, and f are as defined herein, comprising (a) contacting an aqueous $Sb_2O_3$ slurry with $HNO_3$ and one or more Me compounds, and, optionally, one or more compounds selected from X, Q, or R compounds to form a first mixture; (b) heating and drying the first mixture to form a solid product; and (c) calcining the solid product to form the catalyst, the catalysts prepared by the process, and the use of the catalysts in ammoxidation and oxidation processes. The catalysts of the invention are particularly useful for the production of acrylonitrile from propylene, ammonia, and an oxygen-containing gas.

30 Claims, No Drawings

PROCESS FOR PREPARING A CATALYST FOR THE OXIDATION AND AMMOXIDATION OF OLEFINS

BACKGROUND OF THE INVENTION

This invention relates to a process for the production of antimonate-based mixed metal oxide catalysts and the catalysts produced therefrom. This invention further relates to use of the antimonate-based mixed metal oxide catalysts of the invention in reactions for the ammoxidation or oxidation of organic compounds.

It is known that antimony-containing metal oxide catalysts, specifically those comprising the oxides of antimony and at least one metal selected from the group consisting of iron, cobalt, nickel, tin, uranium, chromium, copper, manganese, titanium, and cerium are useful for the production of aldehydes and carboxylic acids through oxidation of organic compounds, i.e. olefins, the production of dienes, unsaturated aldehydes and unsaturated acids through oxidative dehydrogenation of olefins, and the production of nitriles through ammoxidation of olefins, alcohols and aldehydes.

Various catalytic processes are known for the oxidation or ammoxidation of olefins. Such processes commonly react an olefin or an olefin-ammonia mixture with oxygen in the vapor phase in the presence of a catalyst. For the production of acrolein and acrylonitrile, propylene is the generally used olefin reactant, and for the production of methacrolein and methacrylonitrile, isobutene is the generally used olefin reactant.

Many catalysts are disclosed as suitable in the oxidation and/or ammoxidation of olefins, including those catalysts disclosed in U.S. Pat. Nos. 5,094,990; 4,590,175; 4,547,484; 4,487,850; and 4,413,155. One such catalyst is described in U.S. Pat. No. 4,547,484. This catalyst is represented by the empirical formula:

$$Sb_aU_bFe_cBi_dMo_eO_f$$

wherein a is 1 to 10, b is 0.1 to 5, c is 0.1 to 5, d is 0.001 to 0.1, e is 0.001 to is a number taken to satisfy the valence requirements of Sb, U, Fe, Bi, and Mo in the oxidation states in which they exist in the catalyst. The processes for preparing these catalysts involve the addition of solid, generally powdered, antimony, added as antimony metal or $Sb_2O_3$ to the reactor.

Although the yield and selectivity of the above-described catalysts are generally satisfactory, the commercial utility of a catalyst system is highly dependent upon the cost of the system, the conversion of the reactant(s), the yield of the desired product(s), and the stability of the catalyst during operation. In many cases, a reduction in the cost of a catalyst system on the order of a few cents per pound or a small percent increase in the yield of the desired product represents a tremendous commercial economical advantage. Since it is well known that the economics of acrylonitrile manufacture dictate increasingly higher yields and selectivity of conversion of reactants to acrylonitrile in order to minimize the difficulties attending the purification of the product and handling of large recycle streams, research efforts are continually being made to define new or improved catalyst systems and methods and processes of making new and old catalyst systems to reduce the cost and/or upgrade the activity and selectivity of such catalyst systems. A catalyst having improved reproducibility and homogeneity, and containing substantially less $\alpha\text{-}Sb_2O_4$ while having equivalent or better catalyst performance is desired. The discovery of the improved catalysts of the present invention and the method of preparing the improved catalysts of the present invention is therefore believed to be a decided advance in the state of the art.

SUMMARY OF THE INVENTION

According to the invention, a process for preparing an antimonate-based mixed metal oxide catalyst in a catalytically active oxidized state is provided wherein the catalyst is represented by the empirical formula:

$$Me_aSb_bX_cQ_dR_eO_f$$

wherein Me is at least one element selected from Fe, Co, Ni, Sn, U, Cr, Cu, Mn, Ti, Th, Ce, Pr, Sm, or Nd; X is at least one element selected from V, Mo, or W; Q is at least one element selected from Li, Na, K, Rb, Cs, Be, Mg, Ca, Sr, Ba, Sc, Y, La, Zr, Hf, Nb, Ta, Re, Ru, Os, Rh, Ir, Pd, Pt, Ag, Au, Zn, Cd, Hg, Al, Ga, In, Tl, Ge, Pb, As, or Se; R is at least one element selected from Bi, B, P, or Te; and the subscripts a, b, c, d, e, and f denote atomic ratios and are as follows: a is 0.1 to 15, b is 1 to 100, c is 0 to 20, d is 0 to 20, e is 0 to 10, and f is a number taken to satisfy the valence requirements of the metals present in the catalyst in the oxidation states in which they exist in the catalyst, comprising:

(a) contacting an aqueous $Sb_2O_3$ slurry with $HNO_3$ and one or more Me compounds, and, optionally, one or more compounds selected from X, Q, or R compounds to form a first mixture;

(b) heating and drying the first mixture to form a solid product; and (c) calcining the solid product to form the catalyst.

Further according to the invention, antimonate-based mixed metal oxide catalysts in a catalytically active oxidized state prepared according to the process of the present invention are provided.

Still further according to the invention, ammoxidation, oxidation, and oxydehydrogenation processes utilizing the antimonate-based mixed metal oxide catalysts of the present invention which are prepared according to the process of the present invention are provided.

BRIEF DESCRIPTION OF THE DRAWINGS

Not Applicable.

DETAILED DESCRIPTION

Catalysts that can be prepared according to the process of the present invention include, but are not limited to, those catalysts having the empirical formulae described in U.S. Pat. Nos. 5,094,990; 4,590,175; 4,547,484; 4,487,850; and 4,413,155, the disclosures of which are incorporated by reference herein in their entirety.

This invention provides an antimonate-based mixed metal oxide catalyst in a catalytically active oxidized state wherein the catalyst is represented by the empirical formula:

$$Me_aSb_bX_cQ_dR_eO_f$$

wherein Me is at least one element selected from Fe, Co, Ni, Sn, U, Cr, Cu, Mn, Ti, Th, Ce, Pr, Sm, or Nd; X is at least one element selected from V, Mo, or W; Q is at least one element selected from Li, Na, K, Rb, Cs, Be, Mg, Ca, Sr, Ba, Sc, Y, La, Zr, Hf, Nb, Ta, Re, Ru, Os, Rh, Ir, Pd, Pt, Ag, Au, Zn, Cd, Hg, Al, Ga, In, Tl, Ge, Pb, As, or Se; R is at least one element selected from Bi, B, P, or Te; and the subscripts a, b, c, d, e, and f denote atomic ratios and are as follows:

a is 0.1 to 15, preferably 0.1 to 10, and more preferably 0.1 to 5;

b is 1 to 100, preferably 1 to 50, and more preferably 1 to 10;

c is 0 to 20, preferably 0.001 to 5, more preferably 0.001 to 0.2, and most preferably 0.01 to 0.2;

d is 0 to 20, and preferably 0 to 10;

e is 0 to 10, preferably 0.001 to 5, more preferably 0.001 to 0.2, and most preferably 0.01 to 0.2; and f is a number taken to satisfy the valence requirements of the metals present in the catalyst in the oxidation states in which they exist in the catalyst.

A particularly preferred catalyst of the invention is represented by the empirical formula:

$$U_{a'}Fe_aSb_bMo_cBi_eO_f$$

wherein a and a' are independently selected from 0.1 to 5, preferably 0.1 to 1; b is 1 to 10, preferably 1 to 5; c is 0.001 to 0.2, preferably 0.01 to 0.1; and e is 0.001 to 0.2, preferably 0.01 to 0.05.

The catalysts of the present invention are prepared by an improved process comprising:

(a) contacting an aqueous $Sb_2O_3$ slurry with $HNO_3$ and one or more Me compounds, preferably Me oxide or Me nitrate compounds, and, optionally, one or more compounds selected from X, Q, or R compounds to form a first mixture;

(b) heating and drying the first mixture to form a solid product; and (c) calcining the solid product to form the catalyst.

The preferred Me elements are selected from Fe, Co, Ni, Sn, U, Cr, Cu, Mn, Ti, Th, or Ce, with Fe and U being currently most preferred. The preferred R elements are selected from Bi, Te, or P, with Bi being currently most preferred. The currently preferred X element is Mo. The preferred Q elements are selected from Mg, Ca, Zr, Nb, Ta, Zn, Al, Ga, and Pb. When more than one element of a particular group, i.e. more than one Me element, is present in the catalyst, the subscript of each element of a particular group is independently selected according to the definition of that specific subscript. For example, if Me is selected to include U and Fe, each subscript "a" is independently selected from 0.1 to 15, preferably 0.1 to 10, and more preferably 0.1 to 5.

The compounds containing Me suitable for use in the process of the invention include oxide and nitrate compounds. Examples of suitable Me compounds include, but are not limited to, triuranium octoxdide, uranium dioxide, uranyl nitrate, and ferric nitrate. When Me is iron (III), the Fe compounds also can include $Fe_2(SO_4)_3$, $Fe(OH)_3$ and $FeCl_3$. When Me is iron (III), the preferred Fe compound is ferric nitrate.

Suitable compounds containing elements X, Q, and R for use in the process of the invention include compounds capable of dissolving under acid conditions such as oxide, nitrate, chloride and sulfate compounds, or reaction products thereof. The preferred compounds are oxide and nitrate compounds. For example, the compounds containing elements X, Q, and R can be added as the oxide or nitrate, as a corresponding salt, or optionally added as the oxide or nitrate and reacted in situ with a suitable compound to produce the corresponding salt. Examples of suitable X compounds include molybdenum oxide, tungsten oxide, vanadium oxide, ferric molybdate, ammonium molybdate, ammonium metatungstate, and ammonium metavanadate. Examples of suitable R compounds include bismuth trioxide, bismuth nitrate, tellurium dioxide, phosphoric acid, ammonium salts of phosphoric acid, phosphorus pentoxide, and boric acid. Examples of suitable Q compounds include potassium nitrate, magnesium oxide, magnesium nitrate, zirconiuim oxide, aluminum oxide, aluminum nitrate, zinc oxide, and zinc nitrate.

The process of the present invention requires that a slurry of $Sb_2O_3$ be contacted with $HNO_3$. In the process of the invention, $NHO_3$ can be added to the aqueous $Sb_2O_3$ slurry or the aqueous $Sb_2O_3$ slurry can be added to $NHO_3$. It is currently preferred to add $NHO_3$ to the aqueous $Sb_2O_3$ slurry. The aqueous $Sb_2O_3$ slurry can be prepared and used immediately in the preparation of the catalyst of the invention, or the aqueous $Sb_2O_3$ slurry can be prepared and stored for later use in the preparation of the catalyst of the invention. The aqueous $Sb_2O_3$ slurry can be prepared by any conventional technique known in the art. In addition, commercially available $Sb_2O_3$ slurries can also be used, e.g. colloidal $Sb_2O_3$ is commercially available and would work very well in the process of the invention. It is currently preferred that the aqueous $Sb_2O_3$ slurry be prepared under high shear or mixed under high shear prior to contacting the aqueous $Sb_2O_3$ slurry with the $NHO_3$. The use of the aqueous $Sb_2O_3$ slurry in the process of the present invention results in a catalyst having improved homogeneity and substantially less $\alpha$-$Sb_2O_4$ in the final catalyst while having equivalent or better catalyst performance than the catalysts prepared using powdered antimony oxide.

The first mixture is preferably heated prior to the heating and drying of step (b), preferably before addition of the compound of element X, in order to convert the initial $\alpha$-$Sb_2O_3$ to other crystalline oxides of antimony, including $\beta$-$Sb_2O_3$ and other antimony oxides i.e. at least a portion of the antimony trioxide being converted to higher oxidation states such as antimony tetroxide and antimony pentoxide. It is particularly preferred to utilize this heating step when a uranium oxide is added to the first mixture. The time required to induce formation of the desired crystalline oxides of antimony can vary and will depend, at least in part, on the temperature employed. Generally, a time period of about 1 hour to about 6 hours, preferably about 2 to about 5 hours, at temperatures from about 80° C. to about 110° C. is sufficient.

The catalyst of the present invention can be employed with or without a support. In some applications, it is advantageous to include in the catalyst a support material which functions by providing a large surface area for the catalyst and by creating a harder and more durable catalyst for use in the highly abrasive environment of a fluidized bed reactor. This support material can be any of those commonly proposed for such use, such as, for example, silica, zirconia, alumina, titania, antimony pentoxide sol, or other oxide substrates. From the point of view of availability, cost, and performance, silica is usually a satisfactory support material and is preferably in the form of silica sol for easy dispersion.

The proportions in which the components of the supported catalysts are present can vary widely, but it is usually preferred that the support provides from about 10% to about 90%, and more preferably about 35% to about 65% by weight of the total combined weight of the catalyst and the support. To incorporate a support into the catalyst, the support material is preferably slurried along with the first mixture in water, preferably after the heating step used to form the crystalline oxides of antimony, at an appropriate pH while maintaining slurry fluidity. When the support material is basic, the pH can be about 7 to about 9. When the support material is acidic, such as acidic silica sol, low pH slurries (pH≦4) are desirable. The preparation of the slurry will be dependent on the specific support material used, and such preparation conditions will be readily apparent to those skilled in the art.

The pH of the first mixture is adjusted, if necessary, prior to the heating and drying of step (b). Depending on the specific catalyst being prepared, the pH may need to be adjusted upward or downward.

At this point, the intimately mixed slurry is heated to remove the bulk of the aqueous phase. The concentrated slurry contains a certain amount of water and it is desirable to remove this water by some form of drying process to form a dry catalyst precursor. This can take the form of a simple oven drying process in which the water-containing solid phase is subjected to a temperature that is sufficiently high to vaporize the water and completely dry the solid phase.

An alternate drying process which may be employed is the so-called spray-drying process. In this process, which is preferred for use in the present invention, water-containing solid phase particles are sprayed into contact with hot gas (usually air) so as to vaporize the water. The drying is controlled by the temperature of the gas and the distance the particles travel in contact with the gas. It is generally desirable to adjust these parameters to avoid too rapid drying as this results in a tendency to form dried skins on the partially dried particles of the solid phase which are subsequently ruptured as water occluded within the particles vaporizes and attempts to escape. At the same time, it is desirable to provide the catalyst in a form having as little occluded water as possible. Therefore, where a fluidized bed reactor is to be used and microspheroidal particles are desired, it is advisable to choose the conditions of spray-drying with a view to achieving substantial complete drying without particle rupture.

Following the drying operation, the catalyst precursor is calcined to form the active catalyst. The calcination is usually conducted in air at essentially atmospheric pressure and at a temperature of about 500° C. to about 1150° C., preferably from about 600° C. to about 900° C. The time to complete the calcination can vary and will depend upon the temperature employed. In general the time can be anything up to 24 hours, but for most purposes, a time period from about 1 hour to about 4 hours at the designated temperature is sufficient.

A preferred process for forming the catalysts of the present invention is described hereafter using the currently preferred catalyst of the invention represented by the empirical formula:

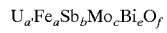

$$U_{a'}Fe_aSb_bMo_cBi_eO_f$$

wherein a and a' are independently selected from 0.1 to 5, b is 1 to 10, c is 0.001 to 0.2, and e is 0.001 to 0.1. While the preferred process is described for the currently preferred catalyst, the preferred process can be utilized with any catalyst of the present invention by choosing the appropriate reaction components and specific reaction conditions.

In a preferred embodiment, this invention provides a process for preparing an antimonate-based mixed metal oxide catalyst in a catalytically active oxidized state, said catalyst represented by the empirical formula:

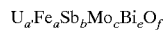

$$U_{a'}Fe_aSb_bMo_cBi_eO_f$$

wherein the subscripts a, a', b, c, e, and f denote atomic rations and are as follows: a is 0.1 to 5, a' is 0.1 to 5, b is 1 to 10, c is 0.001 to 0.2, e is 0.001 to 0.2, and f is number taken to satisfy the valence requirements of Sb, U, Fe, Bi, and Mo present in said catalyst in the oxidation states in which they exist in said catalyst, comprising:

(a) contacting an aqueous $Sb_2O_3$ slurry with $NHO_3$, oxides or nitrates of bismuth, and oxides or nitrates of uranium to form a first mixture;

(b) heating the first mixture at a temperature and for a time sufficient to induce formation of the desired crystalline oxides of antimony (including β-$Sb_2O_3$ and other antimony oxides, e.g. at least a portion of the antimony trioxide being converted to higher oxidation states such as antimony tetroxide and antimony pentoxide) and form a second mixture;

(c) adding an aqueous solution of a ferric compound to the second mixture to form a third mixture;

(d) adjusting the pH of the third mixture to about 7 to about 8.5, thereby forming a hydrated mixed oxide precipitate in an aqueous phase;

(e) separating the hydrated mixed oxide precipitate from the aqueous phase;

(f) forming an aqueous slurry of the hydrated mixed oxide precipitate component;

(g) adding a molybdate to the hydrated mixed oxide component slurry;

(h) forming the hydrated mixed oxide—molybdate component slurry into dry particles; and (i) calcining the dry particles to form the catalyst.

In the formation of the first mixture, it is currently preferred to contact the $HNO_3$ with the aqueous $Sb_2O_3$ slurry prior to contacting the aqueous $Sb_2O_3$ slurry with the oxides or nitrates of bismuth and uranium. Although the order of addition is not critical, it is currently preferred to add the $HNO_3$ to the aqueous $Sb_2O_3$ slurry. The oxides or nitrates of bismuth and uranium can be added together or separately in either order. It is currently preferred to add the oxides or nitrates of bismuth prior to the oxides or nitrates of uranium. The currently preferred bismuth and uranium compounds are bismuth oxide ($Bi_2O_3$) and triuranium octoxide ($U_3O_8$). If bismuth and uranium oxides are used, it is preferred to add the bismuth oxide, heat the slurry to a temperature of about 60° C., and then begin addition of the uranium oxide. If bismuth and uranium nitrates are used, it is preferred not to heat the slurry until after the addition of both compounds is completed.

The first mixture is heated to form the second mixture, in order to convert alpha-antimony trioxide to beta-antimony trioxide and other crystalline oxides of antimony, at least a portion of the antimony trioxide being converted to higher oxidation states such as antimony tetroxide and antimony pentoxide. The time required to induce formation of the desired crystalline oxides of antimony can vary and will depend, at least in part, on the temperature employed. Generally, a time period of about 1 hour to about 6 hours, preferably about 2 to about 5 hours, at temperatures from about 80° C. to about 110° C. is sufficient.

After the heating period is completed, an aqueous solution of ferric compound, preferably ferric nitrate, e.g. $Fe(NO_3)_3$ $9H_2O$, is added to the second mixture, optionally having been cooled to a temperature of about 40° C. to about 60° C. prior to the ferric compound addition. The pH of the resultant mixture is adjusted to about 7 to about 8.5, such as by using aqueous ammonia. The resulting hydrated mixed oxides precipitate and are then separated from the aqueous phase and thoroughly washed to remove substantially all occluded impurities, most notably ammonium nitrate. The hydrated mixed oxides precipitate component is subsequently reslurried to form an aqueous slurry.

The molybdate may be introduced to the hydrated mixed oxide component slurry as any compound that does not interfere with catalysis or neutralize the catalyst. Ammonium molybdate has been successfully employed to introduce the molybdate, and is currently preferred, being the simplest to prepare (from molybdenum trioxide and aqueous ammonia).

The catalyst of the present invention can be employed with or without a support. In some applications, it is advantageous to include in the catalyst a support material which functions by providing a large surface area for the catalyst and by creating a harder and more durable catalyst for use in the highly abrasive environment of a fluidized bed reactor. This support material can be any of those commonly proposed for such use, such as, for example, silica, zirconia, alumina, titania, antimony pentoxide sol, or other oxide substrates. From the point of view of availability, cost, and performance, silica is usually a satisfactory support material and is preferably in the form of silica sol for easy dispersion.

The proportions in which the components of the supported catalysts are present can vary widely, but it is usually preferred that the support provides from about 10% to about 90%, more preferably about 35% to about 65%, and most preferably about 45% to about 55%, by weight of the total combined weight of the catalyst and the support. To incorporate a support into the catalyst, the support material is preferably slurried along with the molybdate in the hydrated mixed oxide component slurry at an appropriate pH while maintaining slurry fluidity. When the support material is basic, the pH can be about 7 to about 9. When the support material is acidic, such as acidic silica sol, low pH slurries (pH≦4) is desirable. The preparation of the slurry will be dependent on the specific support material used, and such preparation conditions will be readily apparent to those skilled in the art.

The resultant slurry is milled, such as by using a ball mill, for a period of time sufficient to reduce the solid particles to a size less than 10μ diameter. For example, a typical time for slurry milling is about 20 hours. Thereafter, the pH of the slurry is adjusted, if necessary, to about 8 to about 9.

Optionally, the milled slurry can be heated to a suitable temperature, e.g. about 95° C. to about 105° C., and held for a suitable time, e.g. about 2 to about 6 hours. If a slurry heating is used, the heated slurry is milled a second time as described above. The heated slurry can optionally be cooled prior to the milling operation if desired.

At this point, the intimately mixed slurry is dried and calcined as described above to produce the catalyst of the invention.

The catalysts of the invention can be utilized in the ammoxidation and oxidation, of olefins.

Ammoxidation

A wide variety of different reactants can be ammoxidized in accordance with the present invention to produce nitrites. For example, olefins such as propylene, isobutylene, 2-methyl-1-pentene, 1,4-hexadiene, and the like, alcohols such as methanol, t-butyl alcohol, and aldehydes such as acrolein and methacrolein can be readily converted to nitrites in accordance with the present invention. In general, compounds which can be converted to nitrites by the ammoxidation reaction using the catalysts of the present invention include 1 to 9 carbon atom hydrocarbons, unsubstituted or substituted with oxygen or hydroxy. Preferred starting materials are olefins, aldehydes and alcohols containing 1 or 4 carbon atoms.

The general ammoxidation process for converting olefins, alcohols and aldehydes to nitrites is well known. See, for example, U.S. Pat. No. 3,546,138, the disclosure of which is incorporated herein by reference. In general, the ammoxidation reaction is accomplished by contacting the reactant, oxygen and ammonia with a particular catalyst in the vapor phase. The reaction can be carried out in the same manner and under the conditions generally set forth in this patent.

In the most frequently used ammoxidation processes, a mixture of olefin, ammonia, and oxygen (or air) is fed into a reactor and through a bed of catalyst particles at elevated temperatures. Such temperatures are usually in the range of about 400° C. to about 550° C., and preferably about 425° C. to about 500° C., and the pressure is from about 1 atmosphere to about 6 atmospheres (100 kPa to about 600 kPa). The ammonia and olefin are required stoichiometrically in equimolar amounts, but it is usually necessary to operate with a molar ratio of ammonia to olefin in excess of 1 to reduce the incidence of side reactions. Likewise, the stoichiometric oxygen requirement is 1.5 times the molar amount of olefin. The feed mixture is commonly introduced into the catalyst bed at a W/F (defined as the weight of the catalyst in grams divided by the flow of reactant stream in ml/sec. at standard temperature and pressure) in the range of about 2 g-sec/ml to about 15 g·sec/ml, preferably from about 3 g-sec/ml to about 10 g-sec/ml.

The ammoxidation reaction is exothermic and for convenience in heat distribution and removal, the catalyst bed is desirably fluidized. However, fixed catalyst beds may also be employed with alternative heat removal means such as cooling coils within the bed.

The catalyst as prepared by the process of this invention is particularly well adapted for use in such a process in that improved yields of and selectivities to the desired product(s) are experienced due to the unique and novel catalyst preparation procedures employed herein.

Oxidation

As previously indicated, the catalysts of this invention can also be employed in the catalytic oxidation of olefins to various different reaction products.

The reactants used in the oxidation to oxygenated compounds are oxygen and an olefin such as propylene, isobutylene and other olefins having up to three contiguous carbon atoms (i.e. three carbon atoms arranged in a straight chain).

The olefins may be in admixture with paraffinic hydrocarbons, such as ethane, propane, butane and pentane; for example, a propylene-propane mixture may constitute the feed. This makes it possible to use ordinary refinery streams without special preparation.

The temperature at which this oxidation is conducted may vary considerably depending upon the catalyst, the particular olefin being oxidized and the correlated conditions of the rate of throughput or contact time and the ratio of olefin to oxygen. In general, when operating at pressures near atmospheric, i.e., 0.1–10 atmospheres, temperatures in the range of 150° C. to 600° C. may be advantageously employed. However, the process may be conducted at other pressures, and in the case where superatmospheric pressures, e.g., above 10 atmospheres are employed, somewhat lower temperatures are possible. In the case where this process is employed to convert propylene to acrolein, a temperature range of 200° C. to 500° C. has been found to be optimum at atmospheric pressure.

While pressures other than atmospheric may be employed, it is generally preferred to operate at or near atmospheric pressure, since the reaction proceeds well at such pressures and the use of expensive high pressure equipment is avoided, and formation of undesired byproducts and waste is diminished.

The apparent contact time employed in the process is not critical and it may be selected from a broad operable range that may vary from 0.1 to 50 seconds. The apparent contact time may be defined as the length of time in seconds which a unit volume of gas measured under the conditions of reaction is in contact with the apparent unit volume of the catalyst. It may be calculated, for example, from the apparent volume of the catalyst bed, the average temperature and pressure of the reactor, and the flow rates of the several components of the reaction mixture.

The optimum contact time will, of course, vary depending upon the olefin being treated, but in the case of propylene and isobutylene, the preferred contact time is 0.15 to 15 seconds.

A molar ratio of oxygen to olefin between about 0.5:1 to 5:1 generally gives the most satisfactory results. For the conversion of propylene to acrolein, a preferred ratio of oxygen to olefin is from about 1:1 to about 2:1. The oxygen used in the process may be derived from any source; however, air is the least expensive source of oxygen and is preferred for that reason.

Inert diluents such as nitrogen and carbon dioxide, may be present in the reaction mixture.

In carrying out the foregoing ammoxidation and oxidation processes, any apparatus of the type suitable for carrying out oxidation reactions in the vapor phase may be employed. The processes may be conducted either continuously or intermittently. The catalyst may be a fixed-bed employing a large particulate or pelleted catalyst or, in the alternative, a fluid-bed catalyst may be employed.

The following examples illustrating the invention are described in order to facilitate a clear understanding of the invention. It should be understood, however, that the examples, while indicating preferred embodiments, are given by way of illustration only and are not to be construed as limiting the invention since various changes and modifications within the spirit of the invention will become apparent to those skilled in the art from the description.

EXAMPLES

Abbreviations and Source of Material

| | |
|---|---|
| $Sb_2O_3$ | Antimony trioxide - Great Lakes Chemical |
| $HNO_3$ | Nitric acid, 70% A.C.S. reagent grade - VWR Scientific Products |
| $U_3O_8$ | Triuranium octoxide - Starmet Corporation |
| $Bi_2O_3$ | Bismuth oxide - Ferro Corporation |
| $NH_4OH$ | Ammoniuim hydroxide, 28%, A.C.S. reagent grade - VWR Scientific Products |
| $Fe(NO_3)_3$ | Ferric nitrate, 7% Fe solution - Bluegrass Chemicals |
| $SiO_2$ | Silica Sol - Ondeo Nalco |
| $MoO_3$ | Molybdenum trioxide - Climax Molybdenum |

As used herein, the following terms are defined in the following manner:

1. "W/F" is defined as the weight of the catalyst in grams divided by the flow rate of the reactant stream in mL/sec measured at STP, the units being g-sec/mL.

2. "Propylene ($C_3H_6$) conversion" is defined as:

$$\frac{\text{moles } C_3H_6 \text{ in feed} - \text{moles } C_3H_6 \text{ in effluent}}{\text{moles } C_3H_6 \text{ in feed}} \times 100$$

3. "Acrylonitrile (AN) selectivity" is defined as:

$$\frac{\text{moles } AN \text{ in effluent}}{\text{moles } C_3H_6 \text{ in feed converted}} \times 100$$

4. "Acrylonitrile (AN) yield" is defined as:

$$\frac{\text{moles } AN \text{ formed}}{\text{moles } C_3H_6 \text{ feed}} \times 100$$

5. "Catalyst Activity Index (CAI)" is defined as:

$$-\{\ln[1-(\% \text{ conversion}/100)]\} \times 100/\text{catalyst weight}$$

The evaluation of the catalysts of Examples 1–6 was conducted in a fluidized bed reaction vessel having an inside diameter of about 41 mm to determine acrylonitrile selectivity and yield and propylene conversion. The amount of catalyst used in the evaluation ranged between 360 grams and 440 grams and was adjusted in order to get a propylene conversion between 98.5–99.2%. A reactant mixture of 7.7 mole percent propylene ($C_3H_6$), 8.4 mole percent ammonia ($NH_3$), and the balance air was passed upward through the catalyst bed at a rate sufficient to give the value of W/F desired. The bed temperature was maintained at 460° C. and the pressure at about 207 kPa (30 psia).

All catalyst preparation reactions were conducted in a jacketed stainless steel (~10 L) reactor using a heat exchanger and a variable speed agitator (paddle blade impeller, no baffles). In the examples of the invention, $HNO_3$ was charged at a controlled rate using a Cole-Parmer Masterflex® peristaltic pump with a number 16 Norprene® line. A 15 minute $HNO_3$ charge time corresponded to a charge rate of 48.2 mL/min, a 30 minute $HNO_3$ charge time corresponded to a charge rate of 24 mL/min, and a 45 minute $HNO_3$ charge time corresponded to a charge rate of 16 mL/min.

Example 1

A catalyst of the composition $U_1Fe_{2.03}Sb_{5.63}Mo_{0.12}Bi_{0.061}O_f$-50% $SiO_2$ was prepared in the following manner. The reactor was charged with 1324 g water, and the agitator started at 210 rpm. 590 g of $Sb_2O_3$ was charged to the reactor and the reactor contents were stirred for 30 min after completion of the $Sb_2O_3$ addition. The $HNO_3$ charge pump was set for 15 min. addition and 1020 g of $HNO_3$ was charged to the reactor with stirring. After completion of the $HNO_3$ charge, 10.2 g of $Bi_2O_3$ was charged to the reactor. The reactor contents were then heated to 58–60° C. Once the temperature reached 60° C., the reactor temperature controller was set to 88° C. and 201.8 g of $U_3O_8$ was charged to the reactor. Upon completion of the $U_3O_8$ addition, the temperature of the reactor contents was raised to 100° C. and the reactor contents were held at 100° C. for 4 hours. The reactor heating was discontinued, cooling water was applied to the reactor jacket, and 1135 g of deionized (DI) ice was added to the reactor. When the reactor contents reached a temperature of 52° C., 1166 g of a chilled $Fe(NO_3)_3$ solution was charged to the reactor. After completion of the $Fe(NO_3)_3$ addition, the reactor contents were cooled to 32° C. A $NH_4OH$ solution (1349 mL 28%

$NH_4OH/1051$ mL $H_2O$) was prepared and $NH_4OH$ charged to the reactor to adjust the pH. The time at which the reactor contents reached a pH of 5 was recorded, 189 g $H_2O$ were added, and the pH held for 15 min. After the 15 min hold, $NH_4OH$ addition resumed until the pH reached 8. After the pH reached 8, 3026 g $H_2O$ were added and the reactor agitator speed was reduced to 100 rpm. The reactor was allowed to sit overnight.

The hydrated mixed metal oxide precipitate was separated from the mother liquor via vacuum filtration and the wet cake was reslurried in 20 liters of deionized water and filtered again to remove the ammonium nitrate formed during precipitation.

3300 g of washed filtercake was mixed with 2337 g of $SiO_2$ sol and a 3.4 wt % Molybdenum solution, prepared by dissolving 12.05 g $MoO_3$ into a dilute $NH_4OH$ (37 ml 28% $NH_4OH/187$ ml $H_2O$) solution. Additional dilution water was added to lower the solids level of the slurry to 25% by weight. The slurry was ball milled for 20 hours and spray dried at an outlet temperature of 83–85° C. The spray dried particles were then calcined at 400° C. for 1 hour, then at 850° C. for 1 hour to give the final catalyst.

Example 2

A catalyst of the composition $U_1Fe_{2.03}Sb_{5.63}Mo_{0.12}Bi_{0.061}O_f$–50% $SiO_2$ was prepared according to the procedure of Example 1 except the initial reactor agitator speed was 180 rpm, the $HNO_3$ charge pump was set for 30 min. addition, and the reactor agitator speed was increased to 210 rpm after completion of the $Fe(NO_3)_3$ addition.

Example 3

A catalyst of the composition $U_1Fe_{2.03}Sb_{5.63}Mo_{0.12}Bi_{0.061}O_f$–50% $SiO_2$ was prepared according to the procedure of Example 1 except the initial reactor agitator speed was 150 rpm, the $HNO_3$ charge pump was set for 45 min. addition, and the reactor agitator speed was increased to 210 rpm after completion of the $Fe(NO_3)_3$ addition.

Example 4

A catalyst of the composition $U_1Fe_{2.03}Sb_{5.63}Mo_{0.12}Bi_{0.061}O_f$–50% $SiO_2$ was prepared according to the procedure of Example 1 except the $HNO_3$ charge pump was set for 45 min. addition.

Example 5

A catalyst of the composition $U_1Fe_{2.03}Sb_{5.63}Mo_{0.12}Bi_{0.061}O_f$–50% $SiO_2$ was prepared according to the procedure of Example 1 except the initial reactor agitator speed was 150 rpm, and the reactor agitator speed was increased to 210 rpm after completion of the $Fe(NO_3)_3$ addition.

Example 6 (Control)

A catalyst of the composition $U_1Fe_{2.03}Sb_{5.63}Mo_{0.12}Bi_{0.061}O_f$–50% $SiO_2$ was prepared in the following manner. 1020 g of $NHO_3$ and 10.2 g of $Bi_2O_3$ were charged to the reactor and the reactor agitator started at 60 rpm. The reactor contents were then heated to 58–60° C. Once the temperature reached 60° C., the reactor temperature controller was set to 88° C. and 201.8 g of $U_3O_8$ was charged to the reactor. Upon completion of the $U_3O_8$ addition, the temperature of the reactor contents was held at 90° C. to 95° C. for 30 min. 1324 g $H_2O$ were added to the reactor, the reactor contents reheated to 90° C. to 95° C., and the reactor agitator speed increased to 150 rpm. 590 g of $Sb_2O_3$ powder was charged to the reactor. Upon completion of the $Sb_2O_3$ powder addition, the temperature of the reactor contents was raised to 100° C. and the reactor contents were held at 100° C. for 4 hours. The reactor heating was discontinued, cooling water was applied to the reactor jacket, and 1135 g of deionized (DI) ice was added to the reactor. When the reactor contents reached a temperature of 52° C., 1166 g of a chilled $Fe(NO_3)_3$ solution was charged to the reactor. Upon completion of the $Fe(NO_3)_3$ addition, the reactor agitator speed was increased to 210 rpm and the reactor contents were cooled to 32° C. A $NH_4OH$ solution (1349 mL 28% $NH_4OH/1051$ mL $H_2O$) was prepared and $NH_4OH$ charged to the reactor to adjust the pH. The time at which the reactor contents reached a pH of 5 was recorded, 189 g $H_2O$ were added, and the pH held for 15 min. After the 15 min hold, $NH_4OH$ addition resumed until the pH reached 8. After the pH reached 8, 3026 g $H_2O$ were added and the reactor agitator speed was reduced to 100 rpm. The reactor was allowed to sit overnight.

The hydrated mixed metal oxide precipitate was separated from the mother liquor via vacuum filtration and the wet cake was reslurried in 20 liters of deionized water and filtered again to remove the ammonium nitrate formed during precipitation.

3140 g of washed filtercake was mixed with 2499 g of $SiO_2$ sol and a 3.4 wt % Molybdenum solution, prepared by dissolving 12.74 g $MoO_3$ into a dilute $NH_4OH$ (40 ml 28% $NH_4OH/198$ ml $H_2O$) solution. Additional dilution water was added to lower the solids level of the slurry to 25% by weight. The slurry was ball milled for 20 hours and then spray dried at an outlet temperature of 83–85° C. The spray dried particles were then calcined at 400° C. for 1 hour, then at 850° C. for 1 hour to give the final catalyst.

All reactor slurries of the invention (Examples 1–5) appeared more homogeneous than the reactor slurry of the control (Example 6).

Example 7

The performance of the catalysts of Examples 1–6 in the ammoxidation of propylene ($C_3H_6$) to acrylonitrile (AN) was determined by conducting ammoxidation reactions according to the procedure described above. The parameters for the ammoxidation reactions are given in Table 1. The catalyst performance results were determined and are given in Table 2.

TABLE 1

| Catalyst | 1 (inv) | 2 (inv) | 3 (inv) | 4 (inv) | 5 (inv) | 6 (con) |
|---|---|---|---|---|---|---|
| Reaction Temp., ° C. | 460 | 460 | 460 | 460 | 460 | 460 |
| Reaction Pressure, x$10^2$ kPa | 2.07 | 2.07 | 2.07 | 207 | 2.07 | 2.07 |
| Feed Mole Percent, % | | | | | | |
| $C_3H_6$ | 7.7 | 7.7 | 7.7 | 7.7 | 7.7 | 7.7 |
| $NH_3$ | 8.4 | 8.4 | 8.4 | 8.4 | 8.4 | 8.4 |
| Air | Balance | Balance | Balance | Balance | Balance | Balance |
| W/F, g-sec/mL | 3.339 | 3.723 | 3.406 | 3.642 | 3.654 | 4.120 |

TABLE 2

| Example | HNO$_3$ Addition Time, min | Agitator RPM | % CO Yield | % CO$_2$ Yield | % HCN Yield | AN Sel., % | % AN Yield | % C$_3$H$_6$ Conversion | CAI | Charge Wt. (g) |
|---|---|---|---|---|---|---|---|---|---|---|
| 5 (invention) | 15 | 150 | 4.90 | 6.88 | 7.25 | 79.66 | 78.88 | 99.03 | 1.189 | 390 |
| 1 (invention) | 15 | 210 | 4.43 | 5.98 | 7.15 | 80.68 | 79.56 | 98.61 | 1.189 | 360 |
| 2 (invention) | 30 | 180 | 4.93 | 6.77 | 7.49 | 79.39 | 78.50 | 98.88 | 1.110 | 405 |
| 3 (invention) | 45 | 150 | 4.57 | 6.45 | 7.31 | 80.20 | 79.21 | 98.76 | 1.220 | 360 |
| 4 (invention) | 45 | 210 | 4.58 | 6.19 | 7.12 | 80.67 | 79.69 | 98.78 | 1.146 | 385 |
| 6 (control) | N/A | 60/150/210 | 5.13 | 7.00 | 7.30 | 79.28 | 78.55 | 99.09 | 1.067 | 440 |

The results in Table 2 demonstrate that the catalysts of the invention have a higher AN selectivity and are more active, i.e. higher CAI, than the control catalyst, i.e. the catalysts of the invention using the slurry addition of Sb$_2$O$_3$ are improved over the control catalyst using addition of Sb$_2$O$_3$ powder. In addition, CO and CO$_2$ yields are improved over the control catalyst.

The catalysts of Examples 1–6 were analyzed using X-ray diffraction (XRD) using a Philips APD 3600 base XRD instrument equipped with APD 3710 electronics to determine if there were any differences in the crystalline oxide compositions of the final catalyst.

The α-Sb$_2$O$_4$ crystalline phase observed in the control catalyst (Example 6) is more pronounced than in all of the catalysts of the invention (Examples 1–5). The catalysts of the invention show increased levels of AN active antimonate phases, FeSbO$_4$, USbO$_5$, and USb$_3$O$_{10}$, and a decreased level of the α-Sb$_2$O$_4$ crystalline phase relative to the control catalyst (Example 6).

What is claimed is:

1. A process for preparing an antimonate-based mixed metal oxide catalyst in a catalytically active oxidized state, said catalyst represented by the empirical formula:

Me$_a$Sb$_b$X$_c$Q$_d$R$_e$O$_f$ wherein Me is at least one element selected from Fe, Go, Ni, Sn, U, Cr, Cu, Mn, Ti, Th, Ce, Pr, Sm, or Nd; X is at least one element selected from V, Mo, or W; Q is at least one element selected from Li, Na, K, Rb, Cs, Be, Mg, Ca, Sr, Ba, Sc, Y, La, Zr, Hf Nb, Ta, Re, Ru, Os, Rh, Ir, Pd, Pt, Ag, Au, Zn, Cd, Hg, Al, Ga, In, Tl, Ge, Pb, As, or Se; R is at least one element selected from Bi, B, P, or Te; and the subscripts a, b, c, d, e, and f denote atomic ratios and are as follows: a is 0.1 to 15, b is 1 to 100, c is 0 to 20, d is 0 to 20, e is 0 to 10, and f is a number taken to satisfy the valence requirements of the metals present in said catalyst in the oxidation states in which they exist in said catalyst, comprising:

(a) contacting an aqueous Sb$_2$O$_3$ slurry with HNO$_3$ and one or more Me compounds, and, optionally, one or more compounds selected from X, Q, or R compounds under controlled pH conditions to form a first mixture which is substantially free of silica sol;

(b) heating and drying said first mixture to form a solid product; and (c) calcining said solid product to form said catalyst.

2. The process of claim 1 further comprising adding a support material selected from silica, zirconia, alumina, or titania to said first mixture after step (a) of contacting an aqueous Sb$_2$O$_3$ slurry with HNO$_3$ and one or more Me compounds but prior to step (b) of heating and drying said first mixture, wherein said catalyst contains from about 10% to about 90% by weight of said support material based on the total weight of said catalyst.

3. The process of claim 2 wherein said catalyst contains from about 35% to about 65% by weight of said support material based on the total weight of said catalyst.

4. The process of claim 3 wherein said support material is silica sol.

5. An antimonate-based mixed metal oxide catalyst in a catalytically active oxidized state, said catalyst prepared by the process of claim 2.

6. The process of claim 1 wherein c is 0.01 to 10, and e is 0.01 to 5.

7. The process of claim 6 wherein Me is selected from Fe, Co, Ni, Sn, U, Cr, Cu, Mn, Ti, Th, or Ce; and R is selected from Bi, Te, or P.

8. The process of claim 7 wherein Me$_a$ comprises Fe$_a$ and U$_{a'}$, and a and a' are independently selected from 0.1 to 10.

9. The process of claim 8 wherein R is Bi, and X is Mo.

10. The process of claim 9 wherein said catalyst is represented by the empirical formula:

U$_a$Fe$_a$Sb$_b$MO$_c$Bi$_e$O$_f$ wherein a and a' are independently selected from 0.1 to 5, b is 1 to 10, c is 0.001 to 0.2, and e is 0.001 to 0.2.

11. An antimonate-based mixed metal oxide catalyst in a catalytically active oxidized state, said catalyst prepared by the process of claim 10.

12. The process of claim 1 wherein the calcining temperature is from about 500° C. to about 1150° C.

13. The process of claim 12 wherein said calcining temperature is from about 600° C. to about 900° C.

14. An antimonate-based mixed metal oxide catalyst in a catalytically active oxidized state, said catalyst prepared by the process of claim 1.

15. A process for preparing an antimonate-based mixed metal oxide catalyst in a catalytically active oxidized state, said catalyst represented by the empirical formula:

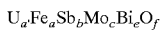

U$_a$Fe$_a$Sb$_b$Mo$_c$Bi$_e$O$_f$ wherein the subscripts a, a', b, c, e, and f denote atomic rations and are as follows: a is 0.1 to 5, a' is 0.1 to 5, b is 1 to 10, c is 0.001 to 0.2, e is 0.001 to 0.2, and f is a number taken to satisfy the valence requirements of Sb, U, Fe, Bi, and Mo present in said catalyst in the oxidation states in which they exist in said catalyst, comprising:

(a) contacting an aqueous $Sb_2O_3$ slurry with $HNO_3$, oxides or nitrates of bismuth, and oxides or nitrates of uranium to form a first mixture;

(b) heating said first mixture at a temperature and for a time sufficient to induce formation of desired crystalline oxides of antimony and form a second mixture;

(c) adding an aqueous solution of a ferric compound to said second mixture to form a third mixture;

(d) adjusting the pH of said third mixture to about 7 to about 8.5, thereby forming a hydrated mixed oxide precipitate in an aqueous phase;

(e) separating the hydrated mixed oxide precipitate from the aqueous phase;

(f) forming an aqueous slurry of the hydrated mixed oxide precipitate component;

(g) adding a molybdate to the hydrated mixed oxide component slurry;

(h) forming the hydrated mixed oxide—molybdate component slurry into dry particles; and (i) calcining the dry particles to form said catalyst.

16. The process of claim 15 wherein a is 0.1 to 1, a' is 0.1 to 1, b is 1 to 5, c is 0.01 to 0.1, and e is 0.01 to 0.05.

17. An antimonate-based mixed metal oxide catalyst in a catalytically active oxidized state, said catalyst prepared by the process of claim 16.

18. The process of claim 15 wherein said first mixture is formed from bismuth trioxide, and triuranium octoxide.

19. The process of claim 18 wherein said third mixture is formed from ferric nitrate.

20. The process of claim 15 wherein said first mixture is heated at a temperature from about 80° C. to about 110° C. for a period from about 1 hour to about 6 hours.

21. The process of claim 15 wherein the molybdate is ammonium molybdate.

22. The process of claim 15 further comprising adding a support material selected from silica, zirconia, alumina, or titania to said hydrated mixed oxide component slurry prior to drying said hydrated mixed oxide—molybdate component slurry, wherein said catalyst contains from about 10% to about 90% by weight of said support material based on the total weight of said catalyst.

23. The process of claim 22 wherein said catalyst contains from about 35% to about 65% by weight of said support material based on the total weight of said catalyst.

24. The process of claim 22 wherein said support material is silica sol.

25. The process of claim 22 wherein said support material is added to said hydrated mixed oxide component slurry prior to adding said molybdate.

26. An antimonate-based mixed metal oxide catalyst in a catalytically active oxidized state, said catalyst prepared by the process of claim 22.

27. The process of claim 15 wherein said dry particles are formed by spray-drying an aqueous slurry.

28. The process of claim 15 wherein the calcining temperature is from about 500° C. to about 1150° C.

29. The process of claim 28 wherein said calcining temperature is from about 600° C. to about 900° C.

30. An antimonate-based mixed metal oxide catalyst in a catalytically active oxidized state, said catalyst prepared by the process of claim 15.

* * * * *

UNITED STATES PATENT AND TRADEMARK OFFICE
CERTIFICATE OF CORRECTION

PATENT NO. : 6,916,763 B2
DATED : July 12, 2005
INVENTOR(S) : Cathy L. Tway

It is certified that error appears in the above-identified patent and that said Letters Patent is hereby corrected as shown below:

Column 13,
Line 45, replace "Go" with -- Co --.
Line 49, replace "Hf Nb" with -- Hf, Nb --.

Signed and Sealed this

Twenty-second Day of November, 2005

JON W. DUDAS
*Director of the United States Patent and Trademark Office*